(12) United States Patent
Graf et al.

(10) Patent No.: US 7,828,806 B2
(45) Date of Patent: Nov. 9, 2010

(54) ACCESSORY FOR IMPLANTING A HIP ENDOPROSTHESIS, AND METHOD FOR MANIPULATING THE SAME

(75) Inventors: Reinhard Graf, Nurau (AT); Martin Imhof, Rotkreuz (CH); René Brack, Rotkreuz (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 1668 days.

(21) Appl. No.: 10/501,004

(22) PCT Filed: Jan. 3, 2003

(86) PCT No.: PCT/EP03/00035

§ 371 (c)(1),
(2), (4) Date: Dec. 13, 2004

(87) PCT Pub. No.: WO03/057087

PCT Pub. Date: Jul. 17, 2003

(65) Prior Publication Data

US 2005/0107799 A1   May 19, 2005

(30) Foreign Application Priority Data

Jan. 10, 2002   (DE) ............................... 102 00 690

(51) Int. Cl.
*A61B 17/58* (2006.01)
(52) U.S. Cl. ...................................................... 606/91
(58) Field of Classification Search .................. 606/91, 606/80, 81, 99, 102, 84–85; 623/22.11–22.12, 623/22.15, 22.18, 22.21; 33/511, 512
See application file for complete search history.

(56) References Cited

U.S. PATENT DOCUMENTS

| | | | | | |
|---|---|---|---|---|---|
| 4,224,698 | A | * | 9/1980 | Hopson | 623/22.11 |
| 4,305,394 | A | * | 12/1981 | Bertuch, Jr. | 606/91 |
| 4,475,549 | A | * | 10/1984 | Oh | 606/91 |
| 4,528,980 | A | * | 7/1985 | Kenna | 606/80 |
| 4,716,894 | A | * | 1/1988 | Lazzeri et al. | 606/91 |
| 4,987,904 | A | * | 1/1991 | Wilson | 600/587 |
| 5,037,424 | A | * | 8/1991 | Aboczsky | 606/91 |

(Continued)

FOREIGN PATENT DOCUMENTS

DE         197 23 620 A1    12/1998

(Continued)

OTHER PUBLICATIONS

International Search Report in the parent PCT Application No. PCT/EP2005/005802 mailed on Sep. 19, 2005, 7 pages.

(Continued)

*Primary Examiner* — Thomas C Barrett
*Assistant Examiner* — Nicholas Woodall
(74) *Attorney, Agent, or Firm* — Benesch, Friedlander, Coplan & Aronoff LLP

(57) ABSTRACT

Accessory for implantation of a hip joint endoprosthesis, with a manipulation cup, a manipulation joint head with means for orienting the manipulation cup in the acetabulum, and with a device to represent the correctly oriented position of the manipulation cup such that by means of this device a bone-milling cutter and an impact instrument can then oriented appropriately for placement of the prosthesis cup.

28 Claims, 15 Drawing Sheets

U.S. PATENT DOCUMENTS

| | | |
|---|---|---|
| 5,098,437 A | 3/1992 | Kashuba et al. |
| 5,474,560 A | 12/1995 | Rohr, Jr. et al. |
| 5,571,111 A | 11/1996 | Aboczky et al. |
| 6,102,915 A | 8/2000 | Bresle et al. |
| 6,231,611 B1 * | 5/2001 | Mosseri .................. 623/22.12 |
| 6,565,575 B2 * | 5/2003 | Lewis ........................ 606/99 |
| 6,743,235 B2 * | 6/2004 | Subba Rao .................. 606/91 |
| 2001/0012967 A1 | 8/2001 | Mosseri et al. |
| 2002/0116007 A1 * | 8/2002 | Lewis ........................ 606/99 |
| 2003/0050645 A1 | 3/2003 | Parker et al. |
| 2003/0153829 A1 * | 8/2003 | Sarin et al. ................ 600/426 |
| 2003/0229356 A1 | 12/2003 | Dye |
| 2004/0097952 A1 | 5/2004 | Sarin et al. |
| 2007/0270783 A1 | 11/2007 | Zumsteg et al. |

FOREIGN PATENT DOCUMENTS

| | | |
|---|---|---|
| DE | 200 21 494 U | 3/2001 |
| EP | 0 229 676 A2 | 7/1987 |
| EP | 0 612 509 A2 | 8/1994 |
| FR | 2 233 972 A | 1/1975 |
| WO | WO 01/91 673 A1 | 12/2001 |
| WO | WO 2004/010882 A | 2/2004 |

OTHER PUBLICATIONS

English Translation of International Preliminary Report on Patentability Report for the parent PCT Application No. PCT/EP2005/005802 mailed on Dec. 28, 2006, 6 pages.

* cited by examiner

ACCESSORY FOR IMPLANTING A HIP ENDOPROSTHESIS, AND METHOD FOR MANIPULATING THE SAME

RELATED APPLICATIONS

This Application is a US National Phase of the International Application No. PCT/EP03/00035 filed Jan. 3, 2003 designating the US and published in German on Jul. 17, 2003 as WO 03/057087, which claims priority of German Patent Application No. 102 00 690.3, filed Jan. 10, 2002.

FIELD OF THE INVENTION

The invention relates to an accessory for implantation of a hip-joint endoprosthesis, as well as to a method for manipulating it, in particular for orienting a bone-milling cutter and an impact instrument to implant a prosthesis cup in the acetabulum.

DESCRIPTION OF THE RELATED ART

When hip endoprostheses are being inserted, the surgeon must proceed through various stages of the operation in which tools are employed; in particular, it is necessary to use a bone cutter in order to mill out the natural acetabulum and thus form a bearing socket within which an artificial cup can be anchored. An impact instrument is also used to drive the cup into place. When using either tool the surgeon must take care that the tools are oriented as precisely as possible, so that the prosthesis cup will ultimately be positioned as intended, with the greatest possible precision.

Important accessories that assist correct positioning and orientation of the tools include so-called navigation systems that function with computer assistance. Obviously, such systems are quite elaborate, and the costs of employing them are correspondingly high. In view of the fact that in medicine, as elsewhere, it is important to reduce costs without any deterioration in the quality of medical care, the present invention is directed toward the objective of providing an accessory for the implantation of a hip-joint endoprosthesis that allows exact positioning of the prosthesis cup in relation to the femur, specifically to the joint head anchored in the femur, with simple mechanical means. During this operation care must be taken to implant the cup in such a way that during every conceivable movement of the femur, a collision between the edge of the cup and the neck of the femur is avoided.

SUMMARY OF THE INVENTION

This objective is achieved in accordance with the invention by an accessory that comprises the following basic elements:
Manipulation cup
Manipulation joint head with means for orienting the manipulation cup in the acetabulum, and
Device to represent the correctly oriented position of the manipulation cup, so that by means of this device it is then possible to orient appropriately a bone-milling cutter and an impact instrument, which are used for placement of the prosthesis cup.

The central point of the accessory in accordance with the invention is thus that by means of a manipulation joint head the manipulation cup is put into a position within the acetabulum such that for all conceivable movements of the femur, a collision between the cup edge and the femoral neck is ruled out. For this purpose, the manipulation joint head is provided with appropriate mechanical or optical orientation means. In a first preferred exemplary embodiment the orientation means is constructed in the form of a shoulder that extends radially outward beyond the spherical part of the manipulation joint head. This shoulder corresponds to the rim of the manipulation cup when the latter is correctly oriented in the acetabulum. When the femur is in its "zero position", the shoulder on the manipulation joint head is spaced apart from the rim of the manipulation-cup opening by an approximately uniform amount over the entire circumference of the latter. The manipulation joint head is fixed to the neck of a manipulation rasp, in particular is set onto it, to assist orientation of the manipulation cup. The manipulation rasp itself is fixed within the femur. Subsequently the operator causes the femur to make all conceivable movements, as follows:

Flexion/extension about the "mediolateral" axis
Abduction/adduction about the "anterior/posterior" axis
Inward/outward rotation about the "craniocaudal" axis.

During this movement sequence the collisions that occur between the shoulder of the manipulation joint head and the rim of the manipulation cup cause the manipulation cup to move into a position such that, after the final implantation of the hip-joint endoprosthesis, collision between the rim of the prosthesis cup and the femoral neck will be reliably avoided.

Another device will of course be needed to represent the position in which the manipulation cup is correctly oriented, after the latter has been removed. With this device it is then possible to orient a bone-milling cutter and an impact instrument for positioning the prosthesis cup within the socket that has been milled out in the acetabulum.

The above-mentioned shoulder on the manipulation joint head can also be defined by shoulder sections distributed approximately uniformly over the circumference of the head. In the extreme case these sections can also be replaced by peg-like projections. Naturally, there must then be a sufficient number of these projections to achieve the orientation of the manipulation cup described above.

As a device to represent the correctly oriented position of the manipulation cup, it is preferable to use a guide rod that can be fixed in the bone and corresponds to a guide device disposed on the manipulation cup. The guide rod can be constructed either as a nail or also as a threaded rod. In the latter case the guide rod comprises a screw thread on the end section to be anchored in the bone, so that it can be screwed into the bone (namely the pelvic bone).

The guide device on the manipulation cup that is associated with the guide rod preferably comprises a component connected to the manipulation cup by way of an arm; this component is in particular a guide block or a guide sleeve with a bore within which the guide rod is guided. Accordingly, after the manipulation cup has been oriented, the guide rod is passed through the guide bore in the guide device disposed on the manipulation cup and is anchored in the bone. Then the manipulation cup is detached from the guide rod. This leaves the guide rod free so that a template can be attached thereto, in particular pushed onto it, for orienting a cutting head or its drive axis in such a way that the orientation of the cutting head corresponds to that of the manipulation cup. When only a single guide rod is available, the orienting template is preferably also rotatable about said rod.

In a preferred implementation of the first exemplary embodiment the orienting template comprises an arm, in particular an angled strap, that can be pushed onto the guide rod and at its free end (i.e., the end opposite the guide rod) bears a direction plate, in particular a plate provided with directional marks with which to orient the milling-cutter drive axle; for such orientation said axle is pivoted while in complete, i.e. gap-free contact with the direction plate and where appropriate also parallel thereto. The marks preferably also provided on the direction plate allow the milling-cutter drive axle to be pivoted parallel to the direction plate into a position aligned with a predetermined directional mark, in particular a predetermined zero position. Accompanying this zero position can be marks for two maximal-tolerance positions, namely ±5°.

So that the direction plate can be held against the drive axle in a gap-free manner even when the milling cutter is in operation, the cutter drive axle is provided with a bush within which it is rotatably seated, and to which the direction plate can be apposed without a gap even during the milling process.

As already mentioned above, an impact instrument is also provided with which to hammer the prosthesis cup into its final position, in a prespecified orientation. The cup impact instrument can likewise be oriented with respect to the abovementioned direction plate of the orienting template, in the same way as is the cutting head or its drive axle. Because the cup impact instrument is known per se, there is no need to describe it further here.

The manipulation cup can also be provided with a guide device by means of which two or more guide rods can be fixed in the bone parallel to one another. In this case the orienting template, which positions the cutting head or its drive axle as well as the cup impact instrument, likewise comprises two or three corresponding through-bores so that it can be pushed onto the guide rods fixed in the bone.

Another implementation of the first exemplary embodiment is characterized by a U-shaped curvature of the direction plate on the orienting template, in which case the space between the two limbs of the plate serves as a receptacle for the milling-cutter drive axle. The axle is preferably seated therein substantially without play, i.e. is parallel to the direction plate, so that the operator need only be concerned with adjusting the drive axle to the zero position. In order better to identify this zero position, the limb of the plate toward the operator, in particular the upper limb, can be provided at its end face with recesses that serve as markings for positioning the milling-cutter drive axle parallel to the direction plate.

Another exemplary embodiment of an accessory in accordance with the invention is characterized in that as a means for orienting the manipulation cup in the acetabulum optical identifiers are provided, e.g. in the form of an indentation or groove that extends over the circumference of the spherical part of the manipulation joint head. Instead of an indentation or groove, a marking line can be provided. All such markings extend within a plane that is either perpendicular to the central axis of the joint head or set at a predetermined angle thereto. In the first case the manipulation cup is correctly oriented when the marking becomes visible above the edge of the manipulation cup. In the second case the orientation of the manipulation cup is anatomically correct when the marking is undetectable on all sides, i.e. over the entire circumference of the manipulation cup.

In each case the manipulation joint head is fixed to the neck of a manipulation rasp in such a way that the central axis of the joint head coincides with the neck axis.

In a third exemplary embodiment the means for orienting the manipulation cup in the acetabulum is a circumferential shoulder extending outward from the joint head in a plane perpendicular to the central axis of the head, combined with a receptacle for the neck of a manipulation rasp, which is positioned at an angle to the central axis of the joint head such that its long axis is parallel to the axis of the femoral neck.

In the case of this exemplary embodiment, the manipulation cup is correctly oriented when the circumferential shoulder on the manipulation joint head is flush with the outer annular surface around the circumference of the manipulation cup.

As a device to represent the correct orientation of the manipulation cup, it i's also possible to use separate fixation rods that extend through a device for holding the manipulation cup. These fixation rods are provided with helically threaded end sections, which can be screwed into the bone so as to anchor the rod therein. In this case it is preferable for a guide rod to be connectable to the aforementioned holding device, in such a way that the guide rod extends approximately parallel to the central axis of the manipulation cup. Then it is possible to attach to this guide rod a guide element that serves to guide a milling-cutter drive axle or a cup impact instrument. The guide element ensures that the orientation of the cutter drive axle and the impact instrument corresponds to that of the manipulation cup.

Regarding further details of this embodiment, reference is made to the relevant subordinate claims.

In the following, exemplary embodiments of the accessory in accordance with the invention, i.e. an instrument for the orientation of manipulation cups, is explained in greater detail with reference to the attached drawings, which illustrate the following objects and actions:

DETAILED DESCRIPTION OF THE PREFERRED EMBODIMENT

Figure 1:
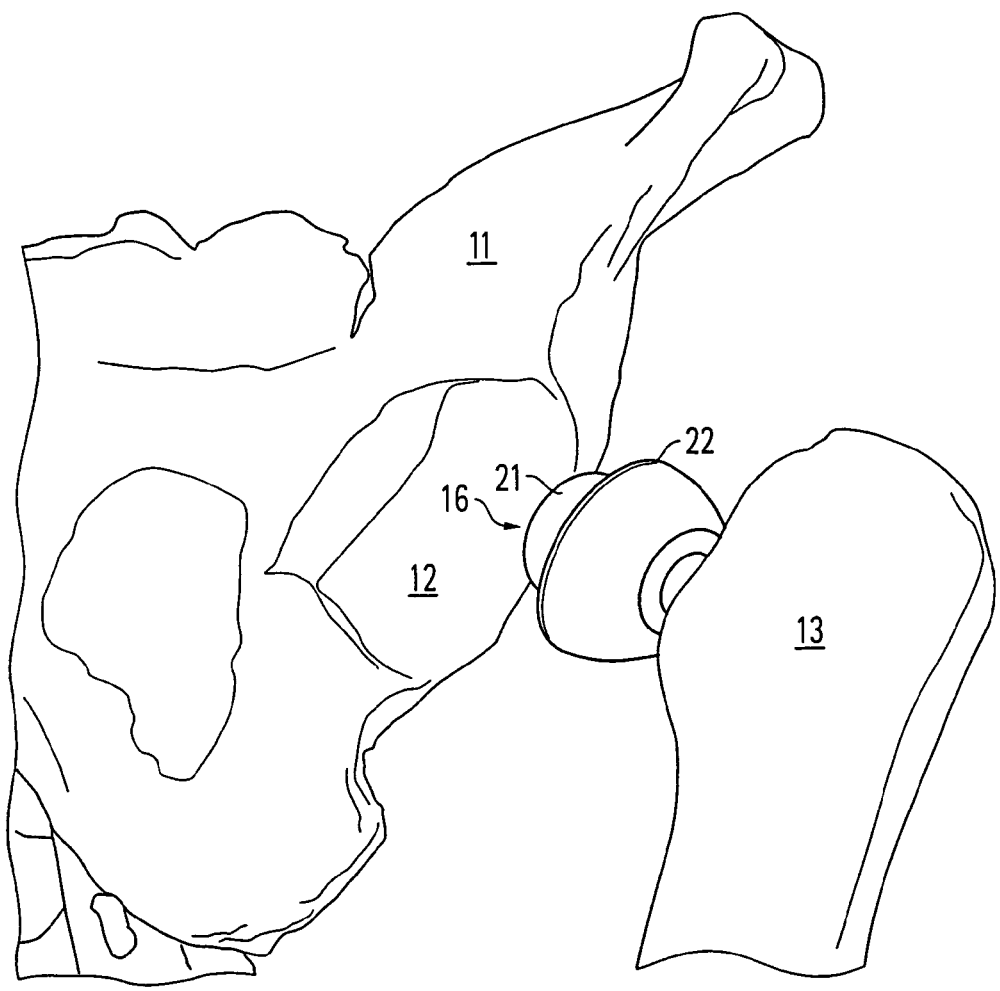
FIG. 1 manipulation joint head fixed to the neck of a manipulation rasp that is placed within the femur, shown in position with respect to the natural acetabulum.
Figure 2:
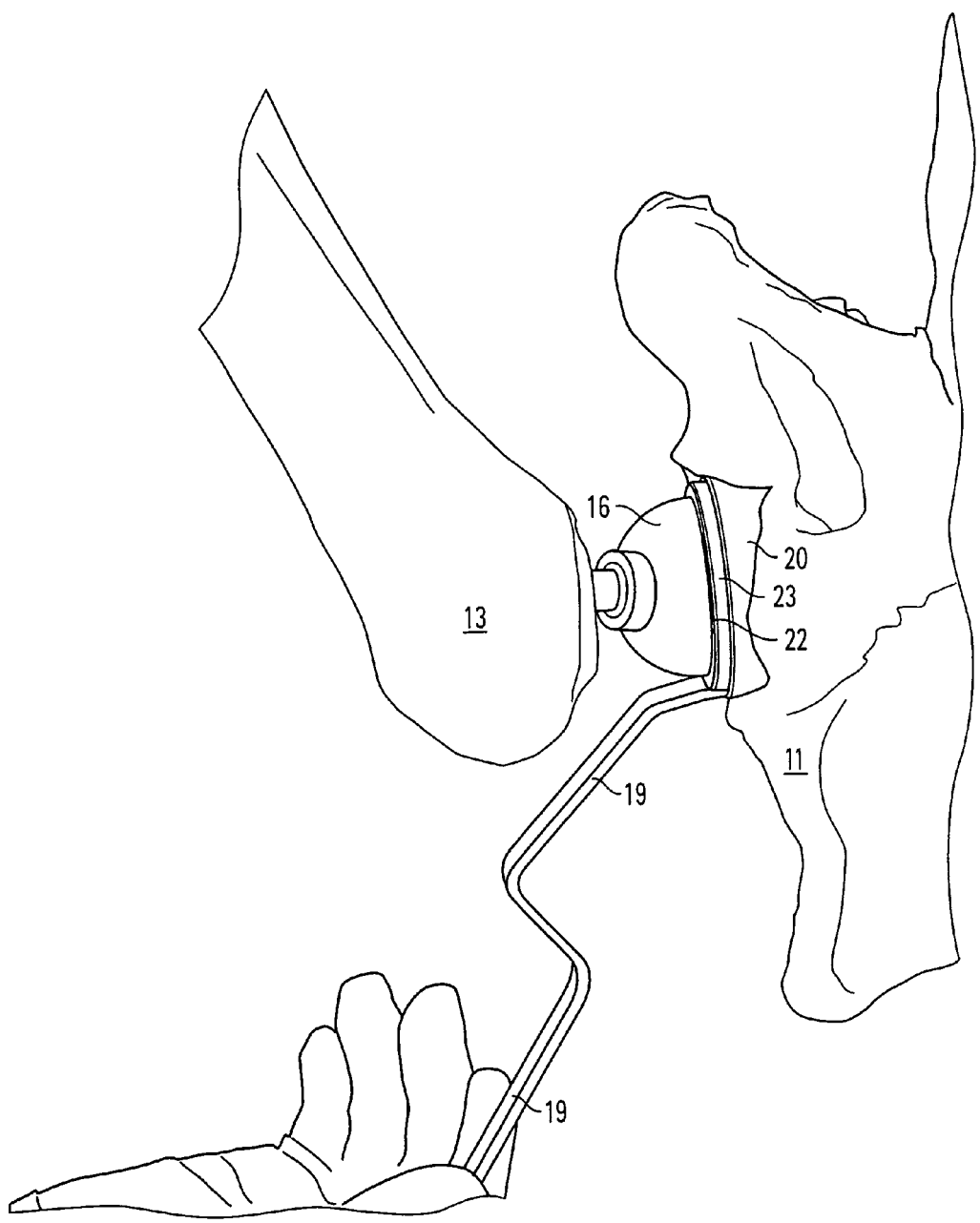
FIG. 2 orienting a manipulation cup placed in the acetabulum by means of the manipulation joint head according to FIG. 1.
Figure 10:
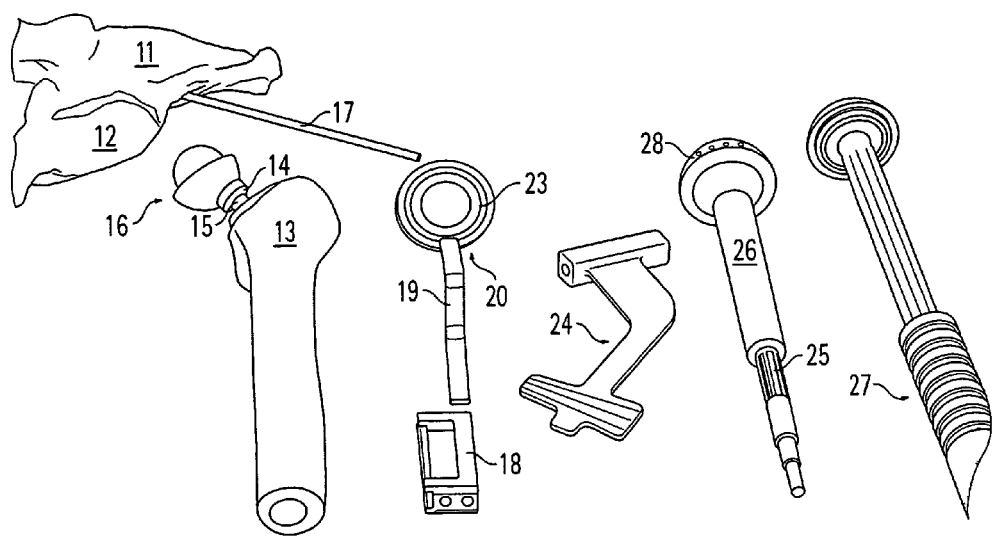
FIG. 10 the complete set of instruments for implantation of a hip-joint endoprosthesis, viewed in perspective.

Prior to consideration of the individual steps, for a first exemplary embodiment the complete set of instruments for anatomically correct implantation of a hip-joint endoprosthesis will be described with reference to FIG. 10, which shows the following parts (from left to right):
- 11 Pelvic bone
- 12 Acetabulum
- 13 Proximal section of a femur, within which a manipulation rasp (not shown in detail) is fixed
- 14 Proximal end of the manipulation rasp placed within the femur
- 15 Prosthesis neck
- 16 Manipulation joint head set onto the prosthesis neck in the conventional way, in particular by means of a "stick-on cone" connection
- 17 Guide rod anchored in the pelvic bone
- 18 Guide block, which can be attached to a manipulation cup to accommodate the guide rod 17
- 19 Manipulation cup with holder strap 19 for the guide block 18
- 24 Orienting template
- 25 Drive axle for milling cutter
- 26 Axle bush
- 27 Cup impact instrument
- 28 Cutting head As shown in FIG. 1, the first step is to tilt the femoral neck back and insert into it, beginning at the plane of resection, a manipulation rasp onto the neck of which a manipulation joint head 16 will be set. The manipulation joint head 16 comprises a spherical part 21, around the circumference of which is a shoulder 22 that extends radially outward. This shoulder 22 is used to establish correspondence with the rim 23 around the opening of the manipulation cup 20, as shown in FIG. 2. In a "zero position" the distance separating the shoulder 22 from the rim 23 of the cup opening is approximately equal around the circumference of the rim 23. Starting from this zero position, the femur 13 together with the manipulation joint head 16 is moved in all anatomically conceivable directions, as described above. As a result of this movement, collisions between the shoulder 22 and the rim 23 of the manipulation cup 20 are very likely to occur at several places, with the consequence that the manipulation cup 20 becomes appropriately oriented within the acetabulum.

Figure 3:
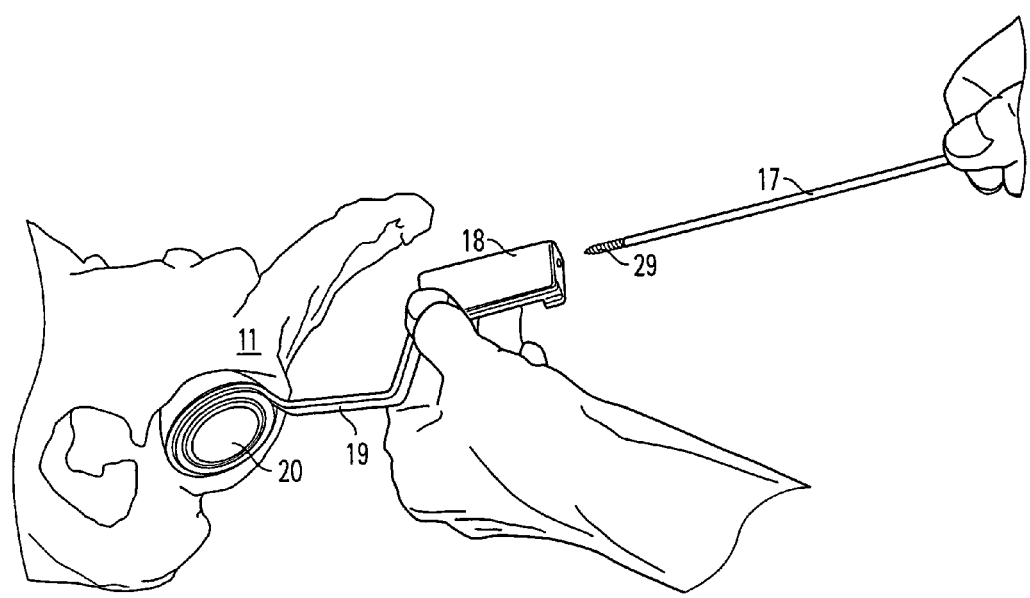
FIG. 3 placement of a guide rod within a guide device associated with the manipulation cup, for future representation of the correct orientation of the manipulation cup, for which purpose the guide rod is anchored in the pelvic bone.
Figure 4:
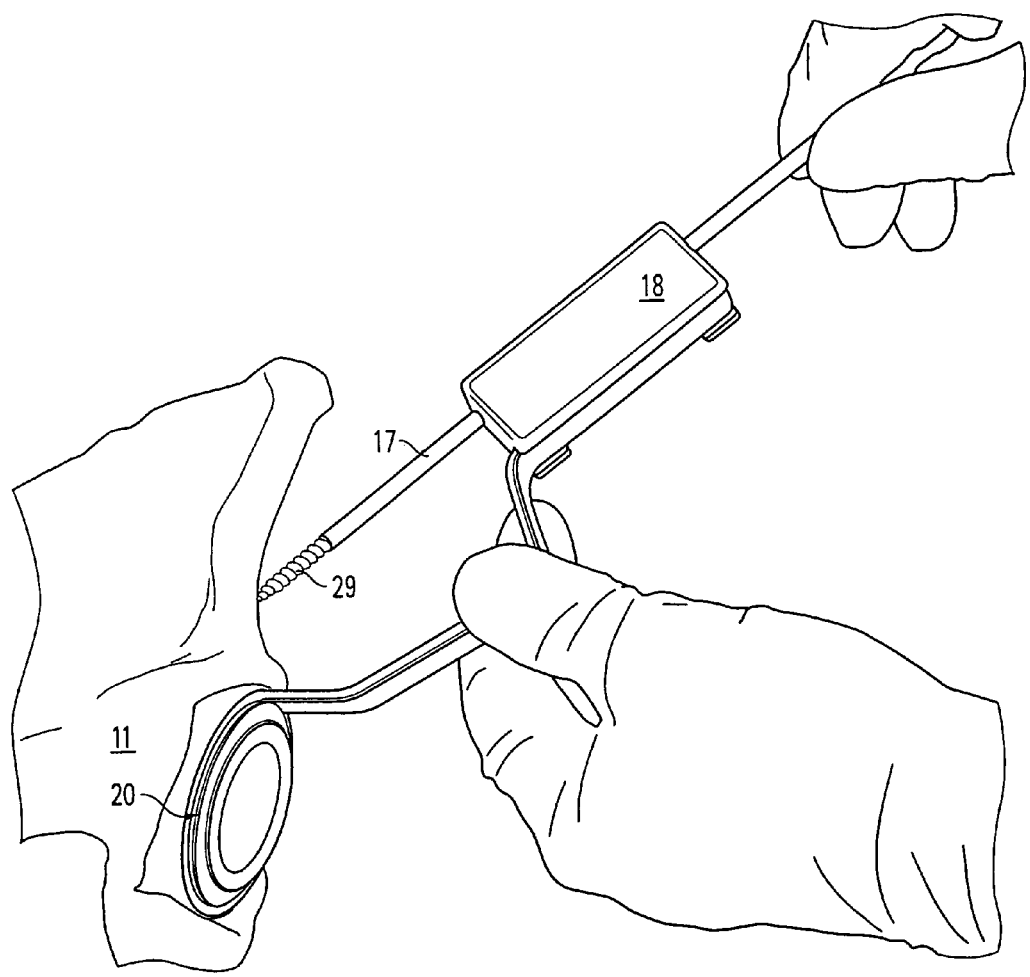
FIGS. 4 and 5 removal of the manipulation cup from the acetabulum and from the guide rod anchored in the bone.
Figure 5:
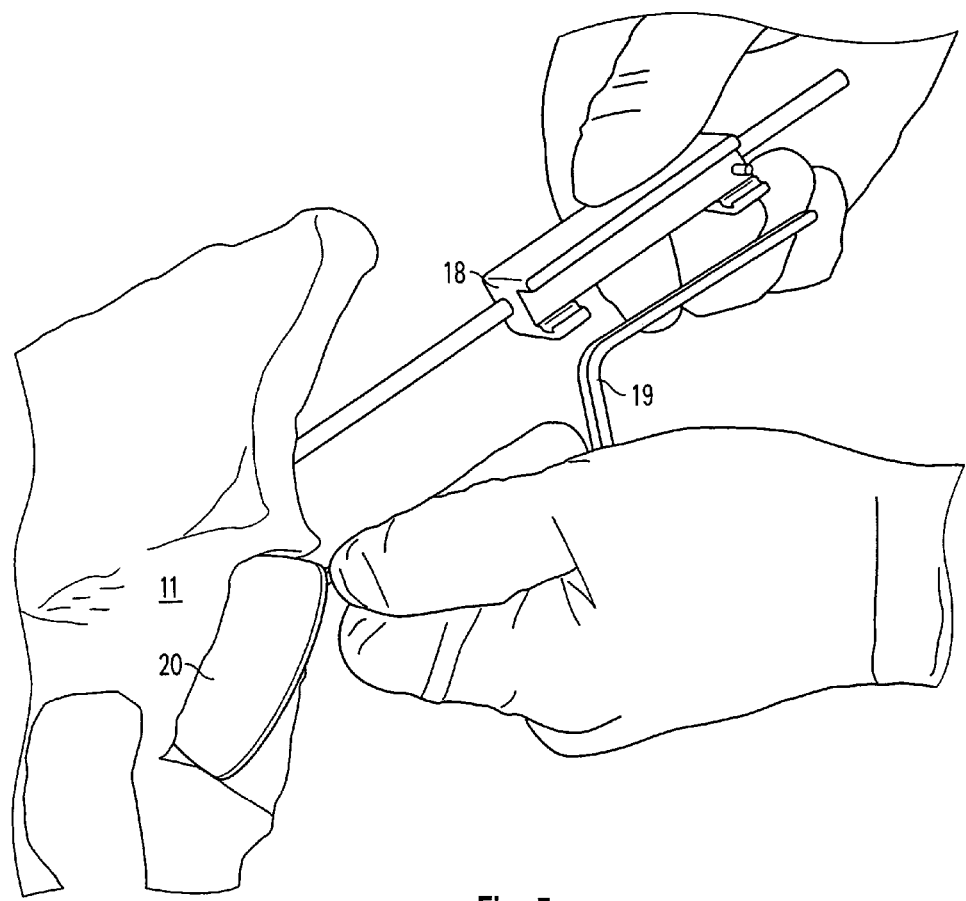

The oriented position of the manipulation cup 20 must be preserved so that both the bone-milling cutter and the impact instrument for the prosthesis cup can be appropriately oriented. For this purpose the manipulation cup 20 is connected by way of a holder strap 19 to a guide device in the form of a guide block 18 comprising a guide bore, the axis of the block being directed toward the pelvic bone 11 and outside the region in which collision with the manipulation cup is possible. Through said guide bore is passed a guide rod 17, as shown in FIGS. 3 and 4. The guide rod 17 has a threaded section 29 at its end that points toward the bone 11, by means of which the guide rod 17 can be screwed into the bone 11 and thus fixed there. The guide rod 17 is, of course, not screwed into the bone 11 until the manipulation cup 20 has been correctly oriented, so that the rod can represent the position of the manipulation cup within the acetabulum. After the guide rod 17 has been fixed within the pelvic bone 11 as just described, the manipulation cup is detached from the guide block 18 as shown in FIG. 5 and removed from the acetabulum.

Figure 6:
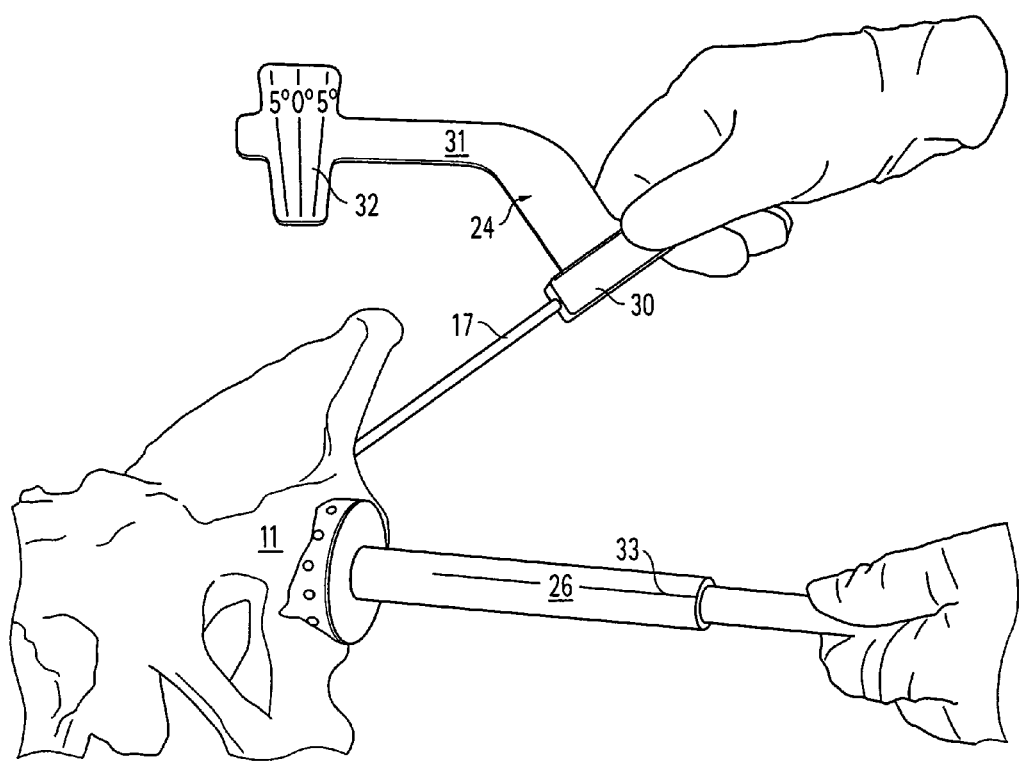
FIG. 6 placement of a bone-milling cutter in the acetabulum, and pushing an orienting template onto the guide rod that is anchored in the bone, to assist orientation of the cutter and/or its drive axle.
Figure 7:
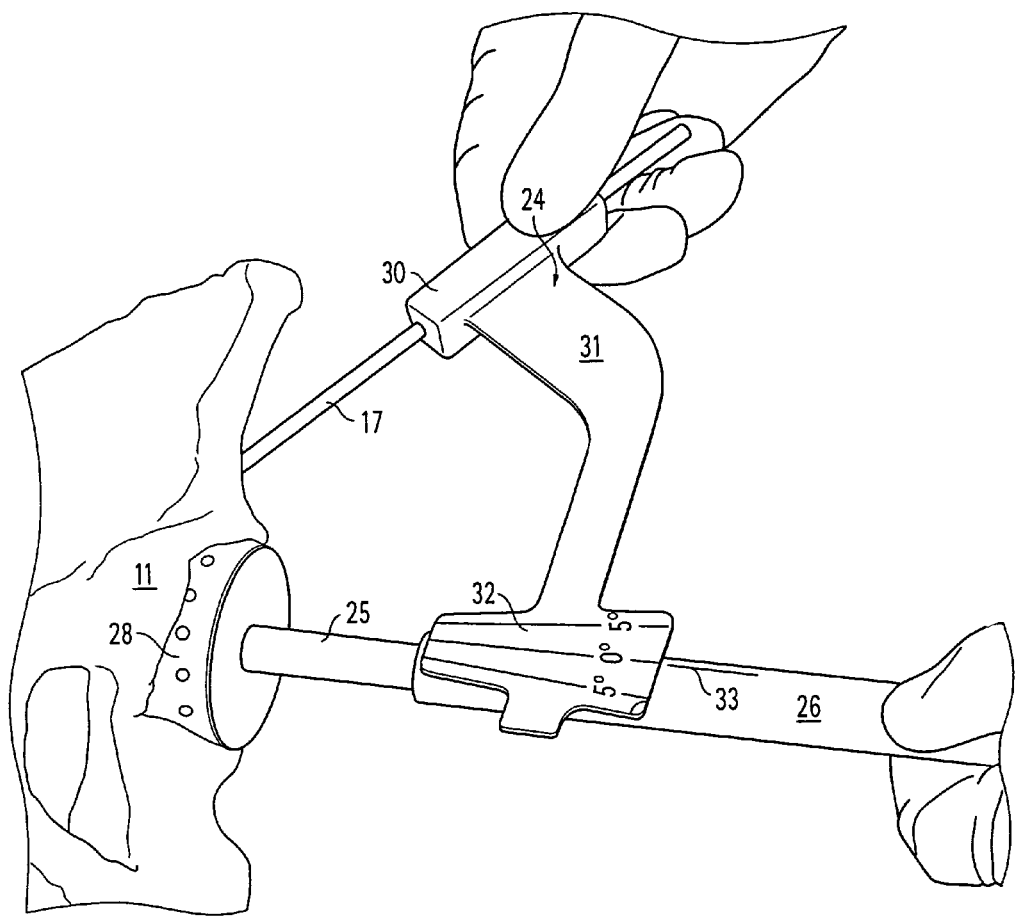
FIGS. 7 and 8 placement of the orienting template and cutter drive axle with respect to one another, and keeping them in this relative position by hand (of the surgeon or an assistant)

Subsequently, as shown in FIGS. 6 and 7, an orienting template 24 is pushed onto the guide rod 17. The orienting template 24 accordingly comprises a guide sleeve fastened to an arm, in this case the angled strap 31. At the free end of the strap 31 a direction plate 32 is formed. This direction plate 32 is provided with marks 33, namely a central zero mark and two tolerance marks at +5°. These marks are identified in FIGS. 6 and 7 by "0°" and "5°".

This orienting template is first used to assist the orientation of a bone-milling cutter with hemispherical cutting head 28 and cutter drive axle 25. To orient the cutting head and its drive axle 25, the template is rotated about the guide rod 17 so as to bring the direction plate 32 into complete, i.e. gap-free contact with the drive axle 25, and then the axle is swivelled parallel to the plate until it is in a position corresponding to a predetermined one of the marks, preferably the zero position "0", as can clearly be seen in FIG. 7.

Figure 8:
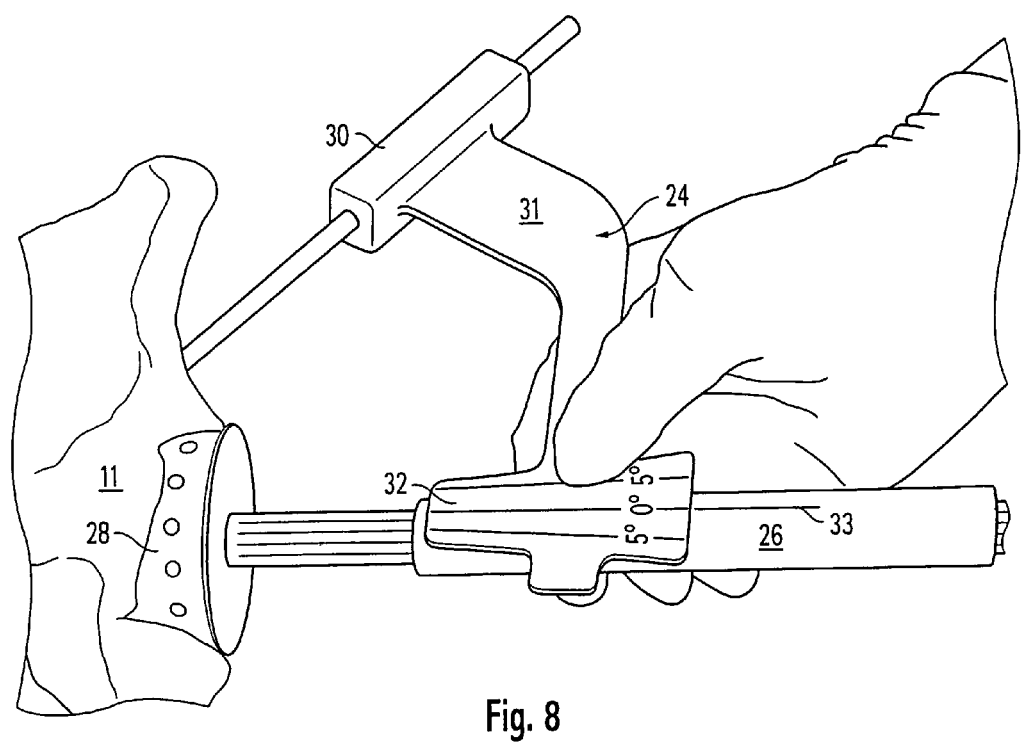

To prevent a collision between direction plate 32 and milling-cutter drive axle 25 while the cutter is in operation, the axle 25 is enclosed in a bush, within which the axle 25 is rotatably seated and onto the surface of which the direction plate 32 can be set and held in gap-free contact during the milling process, as can be seen in FIG. 8.

When the apparatus is positioned according to FIG. 8, the acetabulum can be milled out in the conventional manner. Thanks to the guide rod and the orienting template 24, the hemispherical cutting head 28 is in a position that matches the previously adjusted, anatomically correct position of the manipulation cup 20.

In order better to adjust the cutter drive axle 25 to the zero position, the bush 26 likewise bears a mark 33, a line extending in the long direction. This mark is preferably brought into alignment with the zero mark "0°" on the direction plate 32. Thereafter the milling process can be carried out, to produce a suitable bearing socket into which the prosthesis cup can be inserted. Finally, the prosthesis cup is either screwed into this bearing socket or anchored there by so-called "press-fitting".

Figure 9:
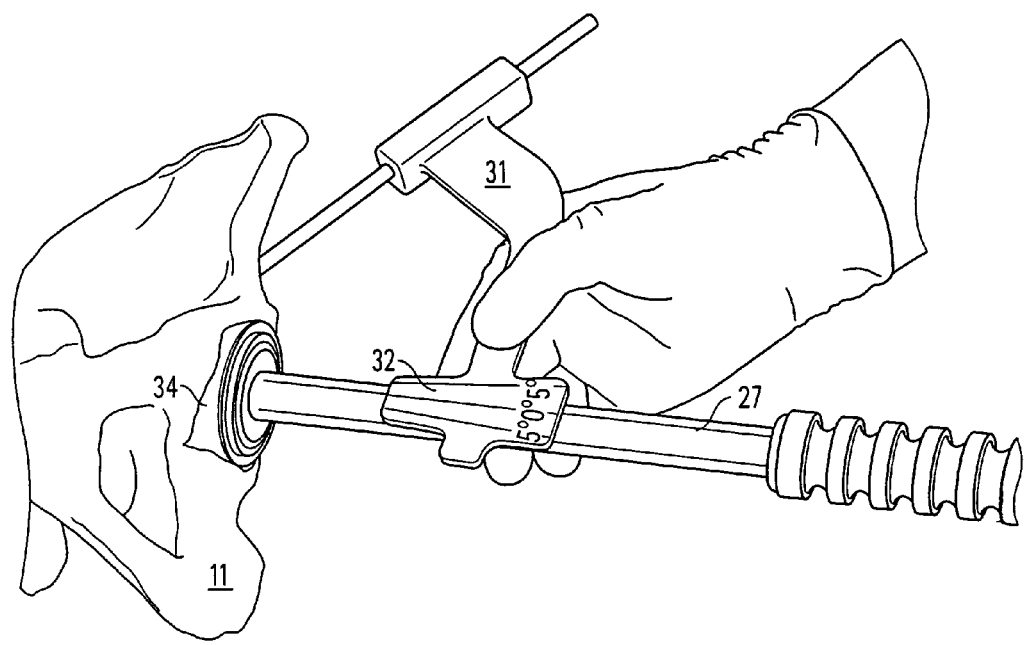
FIG. 9 placement of the orienting template and cup impact instrument with respect to one another, in accordance with the relative positions of orienting template and cutter drive axle as shown in FIGS. 7 and 8.

After milling of the bearing socket in the acetabulum has been completed, the impact instrument 35 (already shown in FIG. 10) is used to hammer in the prosthesis cup 34 that is to be permanently implanted. In this process, of course, care must also be taken that the impact against the prosthesis cup is such that the cup's final position corresponds to that of the manipulation cup 20. Hence the cup impact instrument 27 must be oriented similarly to the bone-milling cutter, i.e. to the cutter's drive axle. The corresponding orientation of the impact instrument 27 is illustrated in FIG. 9. Here, again, the axial structure connecting the impact head to the struck end of the instrument is brought into gap-free contact with the direction plate 32, preferably in alignment with the same marking as was the cutter drive axle. Then it is ensured that when the prosthesis cup 34 is hammered into the previously milled-out bearing socket in the acetabulum, it will be in the anatomically correct orientation.

Figure 11:
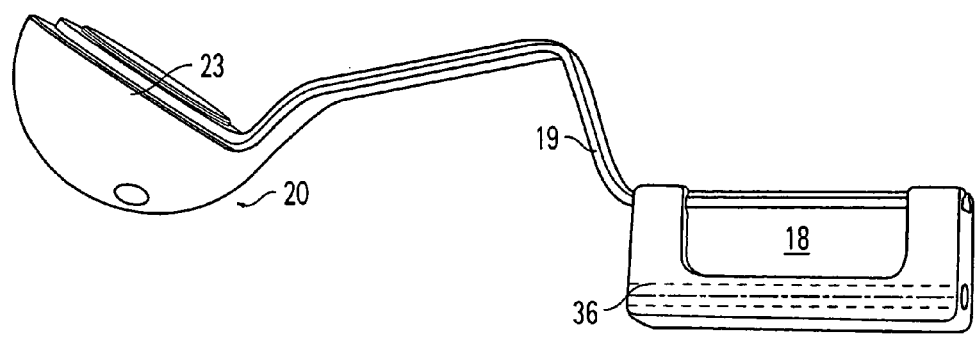
FIG. 11 the manipulation cup together with the guide device for a guide rod that can be anchored in the bone, viewed in perspective.

In FIG. 11 the manipulation cup with guide block for the guide rod 17 is shown again, now in perspective side view. The guide bore in the guide element 30 is indicated by dashed lines and identified by the numeral 36. The guide element 30, as can be seen in FIG. 10 as well as FIG. 5, can be detached from the holder strap 19. The connection between holder strap 19 and guide block is preferably implemented by a catch connector.

Figure 12:
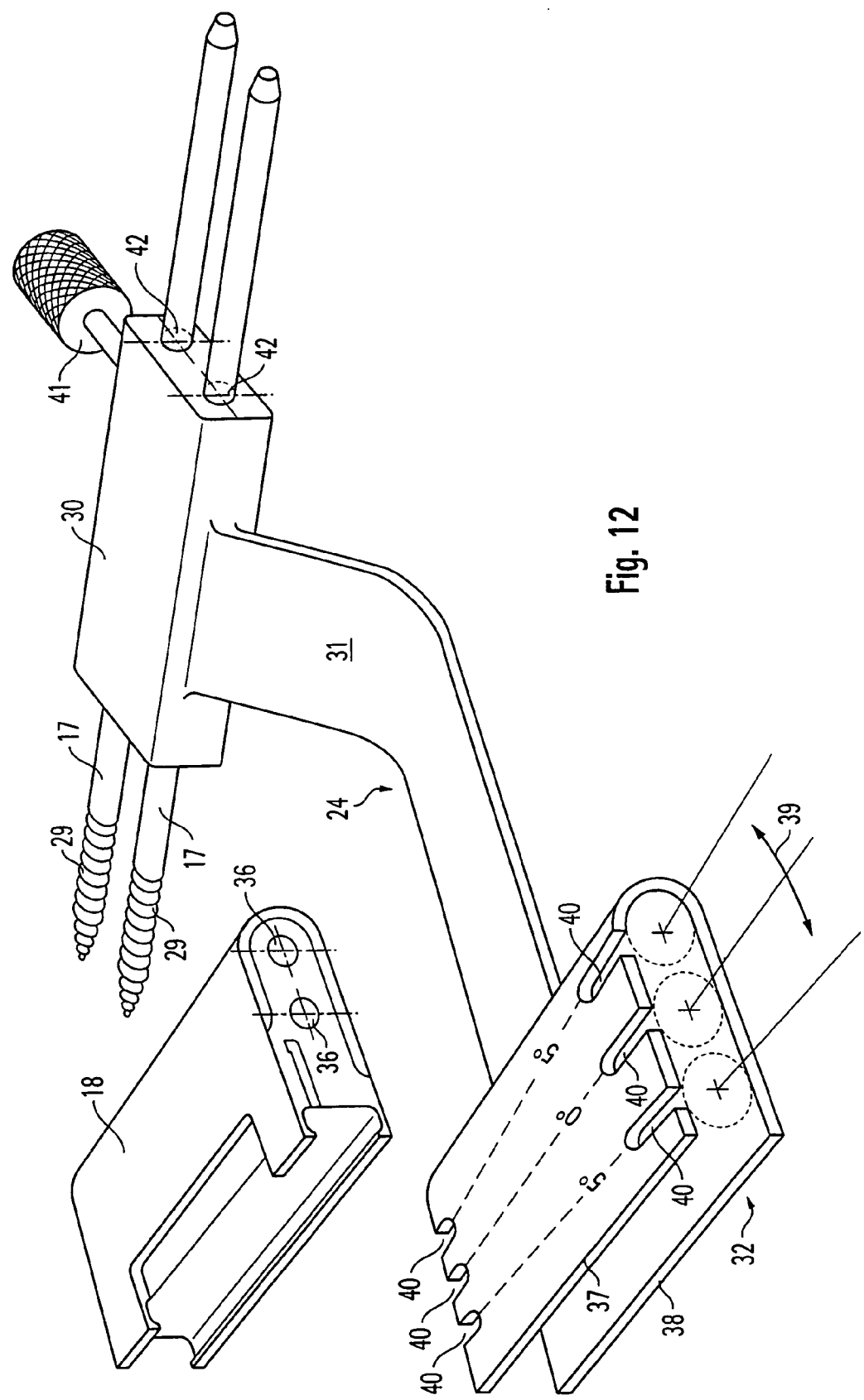
FIG. 12 a modified embodiment of an orienting template, viewed in perspective.

With reference to FIG. 12 a modified embodiment of an orienting template 24 is described, which is distinguished firstly by the fact that the guide element 30 comprises two through-bores 42 to receive two guide rods 17 that extend parallel to one another. Another distinguishing feature of the orienting template 24 shown in FIG. 12 is that the direction plate 32 is bent into a U shape, the space between the two plate limbs 37, 38 serving as a receptacle for the milling-cutter drive axle 25 and/or the cup impact instrument 27. Hence these instruments can be pivoted only in a single plane, parallel to the two plate limbs 37, 38 between which they are held, as indicated by the double-headed arrow 39 in FIG. 12. The arrangement of the two guide rods unambiguously determines the position of the orienting template 24 relative to the acetabulum. Then all that is required of the surgeon is to position the cutter drive axle 25 and/or the cup impact instrument 27 between the two plate limbs 37, 38 in a plane parallel thereto. To facilitate this positioning, recesses 40 are provided in the end faces of the upper plate limb 37. These correspond to the previously mentioned "0°" and "±5°" marks.

The guide element 30 additionally comprises a fixing screw 41 to fix the orienting template 24 to the guide rods 17. Because two guide rods 17 are used here, it is of course also necessary for the guide block 18 associated with the manipulation cup 20 to be constructed with two through-bores 42 for the guide rods 17, as is likewise illustrated in FIG. 12.

The embodiment according to FIG. 12—as explained above—permits correction of the angle of the cutter drive axle and/or the cup impact instrument to be carried out only in one plane. The guide rods 17 can be have different lengths. They preferably, as in previous embodiments, have a screw thread 29 at the end toward the bone.

It is obvious that after the prosthesis cup 34 has been put into place, the guide rods 17 must be removed from the bone. Preferably the guide rods 17 consist of so-called "Kirschner wires".

As mentioned above, the guide block 18 associated with the manipulation cup must also obviously be adapted so that it can be used with two guide rods 17 (two through-bores 36 in the guide block 18 to receive the rods 17, as also shown in FIG. 12).

The manipulation joint head with manipulation rasp must be removed from the femur and replaced by the permanent hip shaft with its joint head. Then the hip joint can be reassembled in the conventional manner. Because of the manipulation and orientation procedures described above, it is then ensured that there will be no collision between the neck of the prosthesis and the rim around the opening of the prosthesis cup 34.

Figure 13:
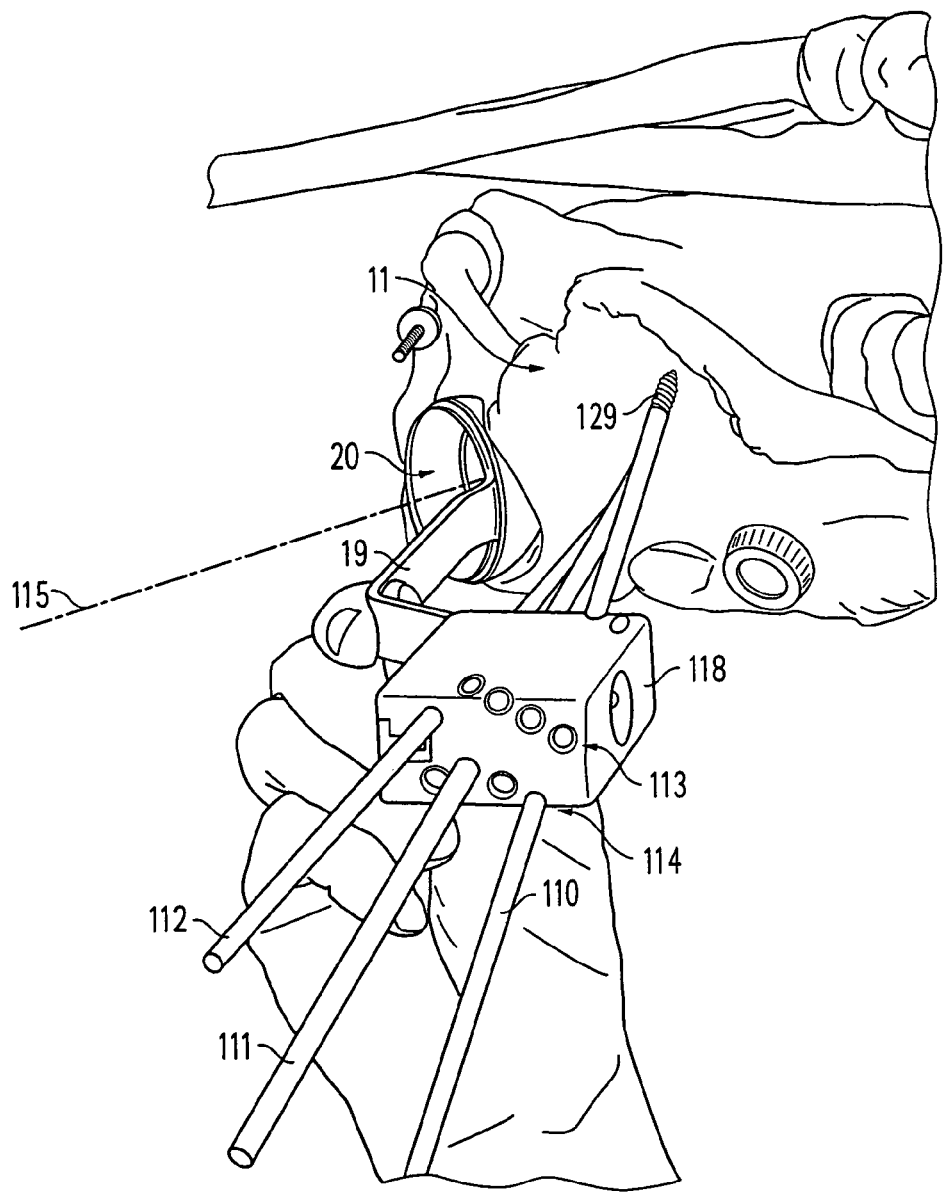
FIG. 13 another embodiment of a device for representing the correct orientation of the manipulation cup, viewed in perspective.

FIG. 13 shows a modified embodiment for a device to represent the oriented position of the manipulation cup 20; this device comprises three fixation rods 110, 111, 112, which extend through a retaining device 118 such that each is at an angle with respect to the others. The fixation rods 110, 111, 112 comprise screw threads 129 on the end sections that are to be anchored in the bone, so that they can be screwed into the bone 11. The retaining device 118 in the present case comprises two rows 113, 114 of holes for the fixation rods 110 ff, so that a sufficient number of holes are available for optimal placement of the fixation rods 110 ff in the bone 11. The manipulation cup 20 is attached to the retaining device 118 by way of the holder strap 19. Furthermore, it is also possible to connect to the retaining device 118 a guide rod 117, in such a way that the guide rod extends approximately parallel to the central axis 115 of the manipulation cup, indicated in FIG. 13 by the reference numeral 115.

Figure 16:
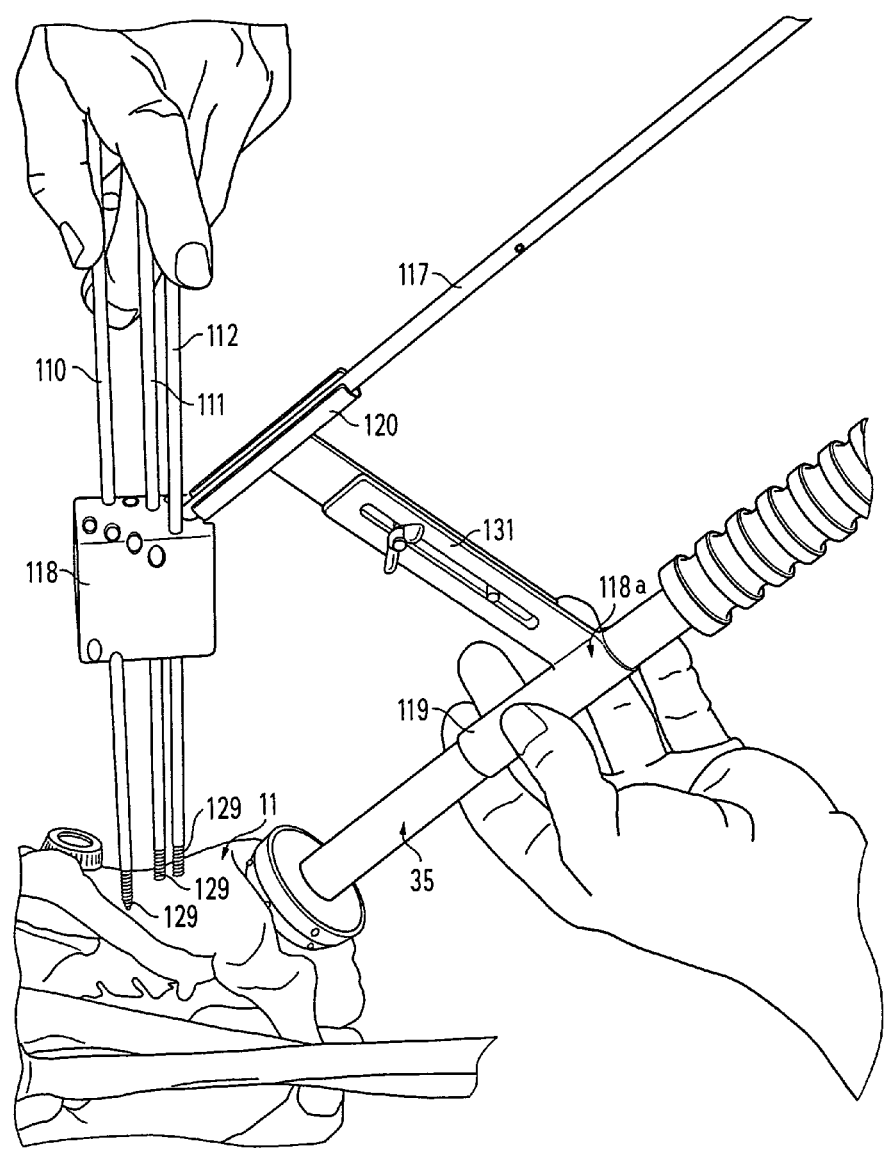
FIG. 16 the arrangement of a guide rod on a manipulation-cup holder, as well as the placement of a guide element on said guide rod for guiding a cup impact instrument, in a position that corresponds to the correctly oriented position of the manipulation cup, in perspective.

To the guide rod 117 there can be attached a guide element 118a in the form of a half-sleeve. The half-sleeve 119 serves to guide a cutter drive axle 25 (not shown in detail in FIG. 16) or a bush 26 enclosing said axle. It additionally serves to guide or orient a cup impact instrument 35, whereby the guide element 118a in the form of a half-sleeve 119 ensures that the orientation of the cutter drive axle and of the cup impact instrument corresponds to that of the manipulation cup 20. In this case the central axis 115 of the manipulation cup coincides with the long axis of the cutter drive axle as well as with the long axis of the cup impact instrument.

The half-sleeve 119 serving as a guide element is connected by way of a flat connector strap 131 to the guide rod 117. The length of the connector strap 131 in the illustrated embodiment can be adjusted. At the end of the connector strap 131 that is associated with the guide rod 117 there is likewise disposed a half-sleeve 120 to serve as an attachment means and sliding shoe. Thus the guide element 118a can be put into position on the guide rod 117 in a simple way, and displaced longitudinally thereon.

Figure 14:
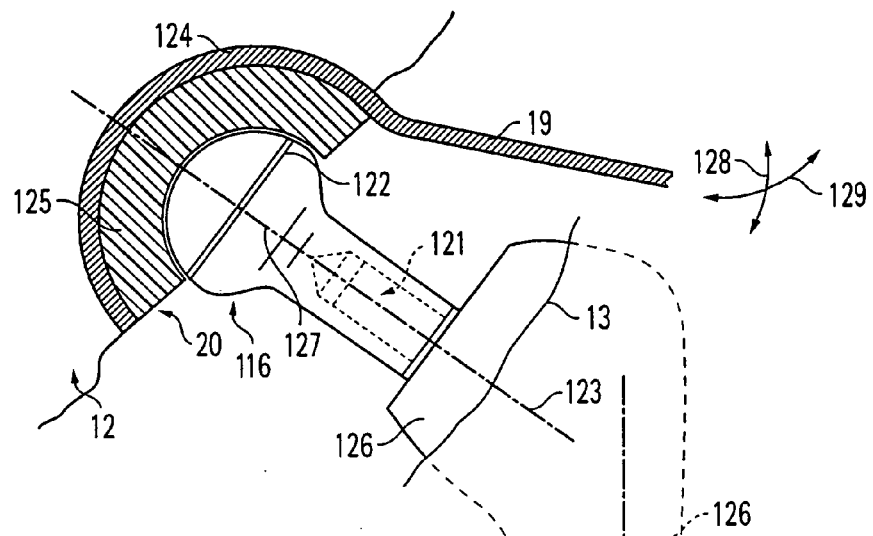
FIG. 14 a second exemplary embodiment of a manipulation joint head in association with a manipulation cup, in schematic section.
Figure 15:
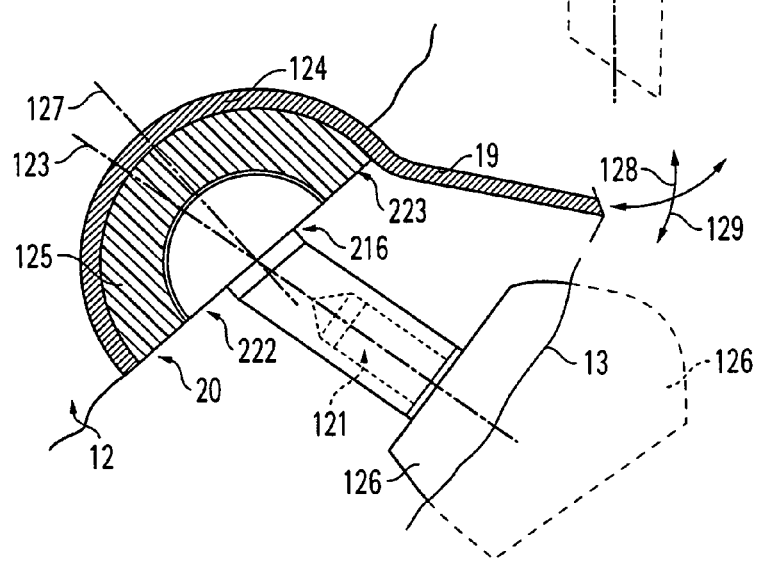
FIG. 15 a third exemplary embodiment of a manipulation joint head in association with a manipulation cup, in schematic section.

FIGS. 14 and 15 show two further, alternative exemplary embodiments of a manipulation joint head 116 and 216, respectively. In both cases the joint heads are mounted on the neck 121 of a manipulation rasp 126. The manipulation rasp 126 has been inserted into the proximal end of a femur 13 (not shown in detail). The long axis of the peg-shaped neck 121 corresponds to the axis of the femoral neck and is identified by the reference numeral 123. The manipulation cup 20 comprises a metallic outer shell 124, onto which has been molded the holder strap 19, as well as an inner shell made of plastic, i.e. an inlay 125. To this extent the structure of the manipulation cup 20 corresponds to that of a prosthesis cup intended for permanent implantation.

In the exemplary embodiment shown in FIG. 14, the means provided for orientation of the manipulation cup 20 in the acetabulum are optical detection means 122. Specifically, the optical detection means 122 is constructed as an indentation or groove extending along the circumference of the spherical part of the manipulation joint head 116. In the present case the path of this groove is perpendicular to the central axis 127 of the joint head, which in the exemplary embodiment according to FIG. 14 coincides with the femoral-neck axis 123.

The indentation 122 extending around the circumference of the spherical part of the manipulation joint head 116 lies within the complementary bearing surface of the manipulation cup 20 when the central axis 127 of the manipulation joint head 116 coincides with the central axis of the manipulation cup. The circumferential indentation 122 does not become visible unless a relative rotation of the manipulation joint head within the manipulation cup 20 occurs. Its invisibility serves as a sign that the manipulation cup 20 is correctly oriented. Preferably the manipulation joint head, i.e. its spherical part, and the manipulation cup comprise markings that correspond to one another, both extending in the circumferential direction, so that the orientation of the manipulation cup about the femoral-neck axis 123 can also be undertaken correctly. The possible movements of the manipulation cup 20, which are those characteristic of a universal joint, are indicated in FIG. 14 by the double-headed arrows 128, 129.

A third exemplary embodiment of means to orient the manipulation cup 20 within the acetabulum 12 is diagrammed in FIG. 15. There the manipulation cup 20 is oriented by the interplay of a circumferential shoulder 222, which extends in a plane perpendicular to the central axis 127 of the joint head, with a receptacle for the neck 121 of the manipulation rasp 126 that extends at an angle to the joint-head central axis 127

(as previously mentioned, the long axis of the neck 121 is parallel to the femoral-neck axis 123).

In this case the manipulation cup 20 has been correctly oriented when said circumferential shoulder 222 is flush with the circumferential ring 223 of the manipulation cup 20, i.e. of the inlay 125.

The two last-mentioned exemplary embodiments thus both comprise optical detection means for orientation of the manipulation cup. They can be handled in a simple manner and function reliably.

In the exemplary embodiment according to FIG. 15, of course, care must be taken that the manipulation joint head is oriented in the prespecified manner with respect to the manipulation rasp 126, i.e. that the joint-head central axis 127 is aimed in a prespecified direction. Only then will it be certain that the objective stated initially is achieved by the final implant.

All the characteristics disclosed in the application documents are claimed as essential to the invention insofar as they are new to the state of the art individually or in combination.

LIST OF REFERENCE NUMERALS

11 Pelvic bone
12 Acetabulum
13 Femur
14 Proximal end of a manipulation rasp
15 Prosthesis neck
16 Manipulation joint head
17 Guide rod
18 Guide block
19 Holder strap
20 Manipulation cup
21 Spherical part of the manipulation joint head
22 Shoulder
23 Opening rim
24 Orienting template
25 Drive axle or shaft for milling cutter
26 Axle bush
27 Cup impact instrument
28 Cutting head
29 Threading
30 Guide sleeve or guide element
31 Angled strap
32 Direction plate
33 Marking
34 Prosthesis cup
36 Guide bore
37 Limb of plate
38 Limb of plate
39 Double-headed arrow
40 Recess
41 Fixing screw
42 Guide bore
110 Fixing rod
111 Fixing rod
112 Fixing rod
113 Row of holes
114 Row of holes
115 Central axis of manipulation cup
116 Manipulation joint head
117 Guide rod
118 Retaining device
118a Guide element
119 Half-sleeve
120 Half-sleeve
121 Neck of a manipulation rasp
122 Circumferential indentation
123 Neck/femoral-neck axis
124 Outer shell
125 Inlay
126 Manipulation rasp
127 Central axis of joint head
128 Double-headed arrow
129 Double-headed arrow
131 Connector strap
216 Manipulation joint head
222 Circumferential shoulder
223 Circumferential annular surface

What is claimed is:

1. An accessory for implantation of a hip joint endoprosthesis, comprising:
   a manipulation cup;
   a manipulation joint with means for orienting the manipulation cup in an acetabulum;
   a device to represent the correctly oriented position of the manipulation cup, the device consisting of a guide rod that is fixed in a bone and corresponds to a guide device attached to the manipulation cup, such that by means of this device a bone-milling cutting head or an impact instrument can then be oriented appropriately for placement of a prosthesis cup; and
   a template that is fastened to the guide rod, and that is used to orient the cutting head or a drive axle of a milling cutter in such a way that the orientation of the cutting head matches that of the manipulation cup,
   wherein the orienting template comprises an arm, which can be pushed onto the guide rod and at the free end of which is disposed a direction plate, to assist orientation of the cutter drive axle, such that to orient the drive axle the latter is pivoted parallel to the direction plate while in complete, gap-free contact therewith, and
   wherein the manipulation joint comprises a manipulation joint head.

2. The accessory according to claim 1, wherein the manipulation joint head comprises a shoulder that extends radially outward around a spherical part and corresponds to a rim around an opening of the manipulation cup so that the manipulation cup can be oriented within the acetabulum.

3. The accessory according to claim 2, wherein the shoulder is defined by shoulder sections distributed approximately uniformly over the circumference.

4. The accessory according to claim 1, wherein the guide rod comprises a screw thread on the end section that is anchored in the bone, so that said rod can be screwed into the bone.

5. The accessory according to claim 1, wherein the guide device on the manipulation cup comprises a component connected to the manipulation cup by way of an arm and having a bore to receive and guide the guide rod.

6. The accessory according to claim 1, further comprising a bush within which the drive axle is rotatably seated and against the surface of which the direction plate can be brought into complete, gap-free contact that is maintained during the milling process, wherein said bush is set onto the milling cutter drive axle.

7. The accessory according to claim 6, further comprising a cup impact instrument that is oriented with respect to the direction plate of the orienting template in the same way as can the cutting head and its drive axle.

8. The accessory according to claim 7, wherein the manipulation cup comprises a guide device for two guide rods that is fixed in the bone so as to be parallel to one another.

9. The accessory according to claim 8, wherein the template for orienting the cutting head or its drive axle comprises two through-bores by way of which it is pushed onto the guide rods fixed in the bone.

10. The accessory according to claim 1, wherein the direction plate of the orienting template is bent into a U shape, such that the space between the two limbs of the plate serves to contain the cutter drive axle and/or the cup impact instrument.

11. The accessory according to claim 10, wherein the plate limb nearest a surgeon, comprises on its end face recesses to serve as markings for orienting the cutter drive axle and/or the cup impact instrument parallel to the direction plate or to its limbs.

12. The accessory according to claim 11, wherein the manipulation joint head can be fixed to a neck of a manipulation rasp.

13. The accessory of claim 12, wherein said manipulation joint head is set into the neck.

14. The accessory of claim 11, wherein said limb is an upper limb.

15. The accessory according to claim 1, wherein as a means for orienting the manipulation cup in the acetabulum optical detection means are provided.

16. The accessory according to claim 15, wherein the spherical part of the manipulation joint head comprises a marking, selected from an indentation, a groove or the like, that extends at least partially around the circumference, within a plane that is either perpendicular to a central axis of the joint head or is set at a prespecified angle thereto.

17. The accessory according to claim 1, wherein said means for orienting the manipulation cup in the acetabulum is a circumferential shoulder that extends outward from the joint head in a plane perpendicular to its central axis, in combination with a receptacle that is inclined at an angle to the central axis of the joint head and contains a neck of a manipulation rasp, the long axis of which extends parallel to a femoral neck axis.

18. The accessory according to claim 1, wherein as a device to represent the correctly oriented position of the manipulation cup at least one, of three fixation rods is provided, which extends through a holding device for the manipulation cup.

19. The accessory according to claim 18, wherein at least one of the fixation rods comprises a screw thread on the end section to be anchored in the bone, so that it is screwed into the bone 3.

20. The accessory according to claim 18, wherein to the holding device is connected a guide rod in such a way that the latter extends approximately parallel to a central axis of the manipulation cup.

21. The accessory according to claim 20, further comprising a guide element for a cutter drive axle or a bush enclosing the axle, as well as for a cup impact instrument, such that the guide element is attached to or set onto the guide rod and ensures that the orientation of the drive axle and of the impact instrument corresponds to that of the manipulation cup.

22. The accessory according to claim 21, wherein the guide element is a sleeve or half-sleeve disposed on a connector strap or similar connecting element.

23. The accessory according to claim 22, wherein the length of the connector strap is adjustable.

24. The accessory of claim 1, wherein said template is pushed onto said guide rod.

25. The accessory of claim 1, wherein said arm is an angled strap.

26. The accessory of claim 1, wherein said direction plate has marks (0.degree.;.+−0.5.degree.).

27. The accessory of claim 26, wherein the drive axle is pivoted parallel to the direction plate into a position corresponding to a specified mark (0.degree.; .+−0.5. degree.).

28. The accessory of claim 27, wherein said specified mark is zero position.

* * * * *

UNITED STATES PATENT AND TRADEMARK OFFICE
CERTIFICATE OF CORRECTION

PATENT NO. : 7,828,806 B2  
APPLICATION NO. : 10/501004  
DATED : November 9, 2010  
INVENTOR(S) : Graf et al.

Page 1 of 1

It is certified that error appears in the above-identified patent and that said Letters Patent is hereby corrected as shown below:

In Col. 3, line 36, "better to" should read --to better--;

In Col. 4, line 5, "i's" should read --is--;

In Col. 6, line 35, "better to" should read --to better--;

In Col. 7, line 59, "fixation rods 110 ff" should read --fixation rods 110--;

In Col. 7, line 61, "fixation rods 110 ff" should read --fixation rods 110--;

In Claim 7, at col. 10, line 64, "can" should be deleted;

In Claim 19, at col. 12, line 8, "bone 3" should read --bone--;

In Claim 26, at col. 12, line 30, "0.degree.; .+-0.5.degree." should read --0°; ± 5°--; and In Claim 27, at col. 12, line 33, "0.degree.; .+-0.5.degree." should read --0°; ± 5°--.

Signed and Sealed this  
Eleventh Day of January, 2011

David J. Kappos  
*Director of the United States Patent and Trademark Office*